(12) United States Patent
Huang

(10) Patent No.: US 11,980,569 B2
(45) Date of Patent: May 14, 2024

(54) MULTI-FUNCTION HEATED GARMENT CAPABLE OF PERFORMING MULTIDIRECTIONAL PHYSICAL THERAPY

(71) Applicant: GUANGDONG LAIJUN ELECTRONIC TECHNOLOGY CO., LTD., Dongguan (CN)

(72) Inventor: Wanglai Huang, Dongguan (CN)

(73) Assignee: GUANGDONG LAIJUN ELECTRONIC TECHNOLOGY CO., LTD., Dongguan (CN)

( * ) Notice: Subject to any disclaimer, the term of this patent is extended or adjusted under 35 U.S.C. 154(b) by 603 days.

(21) Appl. No.: 17/202,292

(22) Filed: Mar. 15, 2021

(65) Prior Publication Data

US 2022/0168135 A1 Jun. 2, 2022

(30) Foreign Application Priority Data

Nov. 30, 2020 (CN) .......................... 202011371889.6

(51) Int. Cl.
*A61F 7/02* (2006.01)
*A61F 7/00* (2006.01)
*G16H 20/30* (2018.01)

(52) U.S. Cl.
CPC ............... *A61F 7/02* (2013.01); *G16H 20/30* (2018.01); *A41D 2200/20* (2013.01); *A61F 2007/0071* (2013.01); *A61F 2007/0077* (2013.01); *A61F 2007/0078* (2013.01); *A61F 2007/0088* (2013.01); *A61F 2007/0093* (2013.01);

(Continued)

(58) Field of Classification Search
CPC ...... A61F 2007/0002; A61F 2007/0018; A61F 2007/0022; A61F 2007/0025; A61F 2007/0026; A61F 2007/0027; A61F 2007/003; A61F 7/007; A61F 2007/0071; A61F 2007/0077; A61F 2007/0078; A61F 2007/0088; A61F 2007/0093; A61F 2007/0233; A61F 2007/0234; G16H 20/30; A41D 2200/20
See application file for complete search history.

(56) References Cited

U.S. PATENT DOCUMENTS 10,004,283 B1 * 6/2018 Baude ................ A41D 13/0051
2001/0047992 A1 * 12/2001 Deangelis .............. H05B 3/342
219/545

(Continued)

*Primary Examiner* — Kaitlyn E Smith
*Assistant Examiner* — Bradford C. Blaise
(74) *Attorney, Agent, or Firm* — Leong C. Lei

(57) ABSTRACT

A multi-function heated garment capable of performing multidirectional physical therapy includes a garment body, a hood, a heating control device, a quick charge source, and a heating load. The heating load includes at least one first carbon fiber heating sheet and a second carbon fiber heating sheet arranged inside the garment body and the hood, respectively. Second electrically conductive buttons provided on the garment body are buckled and electrically connected to first electrically conductive buttons provided on the hood. The hood can be connected or disconnected as required. The carbon fiber heating sheets share the quick charge source and the heating control device. It is safe and convenient to use. It can perform multi-directional heating and infrared physical therapy on various parts of the human body.

9 Claims, 3 Drawing Sheets

(52) U.S. Cl.
CPC .................. *A61F 2007/0233* (2013.01); *A61F 2007/0234* (2013.01)

(56) References Cited

U.S. PATENT DOCUMENTS

| | | | |
|---|---|---|---|
| 2006/0006168 A1* | 1/2006 | Rock | H05B 3/342 |
| | | | 219/545 |
| 2008/0116189 A1* | 5/2008 | Fernandez | H05B 3/342 |
| | | | 219/211 |
| 2013/0131566 A1* | 5/2013 | Bodansky | A61F 5/37 |
| | | | 602/13 |
| 2016/0015559 A1* | 1/2016 | Whitsett | A61F 7/007 |
| | | | 607/108 |
| 2017/0340028 A1* | 11/2017 | Roh | A41D 1/06 |
| 2020/0404987 A1* | 12/2020 | Betkowski | A41D 1/005 |
| 2021/0113366 A1* | 4/2021 | Roberts | A61F 7/02 |
| 2022/0007750 A1* | 1/2022 | Ho | H05B 3/34 |

* cited by examiner

MULTI-FUNCTION HEATED GARMENT CAPABLE OF PERFORMING MULTIDIRECTIONAL PHYSICAL THERAPY

BACKGROUND OF THE INVENTION

1. Field of the Invention

The present invention relates to a heated garment, and more particularly to a multi-function heated garment capable of performing multidirectional physical therapy.

2. Description of the Prior Art

In winter, the thermal performance of ordinary cotton-padded clothing and down jackets cannot fully meet human needs. The coats sold in the market have different thicknesses. In order to keep warm, people often choose thicker and heavier coats. The thermal performance of this jacket is not good, and the appearance of this jacket is unaesthetic. The heavy pressure also makes the wearer feel uncomfortable. Especially for outdoor workers, the heavier the clothing, the more it affects their actions and reduces work efficiency.

For this problem, heated clothing is developed accordingly. However, the conventional heated clothing has a relatively simple structure and function, and cannot perform multi-directional heating and infrared physical therapy on various parts of the human body. At present, it is difficult for a controller of the heated clothing on the market to quickly identify a quick charge source in order to charge a heating load more quickly (with a higher DC voltage), and thus resulting in long heating time and low heating efficiency. In addition, the conventional quick charge source will be in a sleep mode and result in no output current after having been working for a period of time. Therefore, it is necessary to study a solution to solve the above problems.

SUMMARY OF THE INVENTION

In view of the shortcomings of the prior art, the primary object of the present invention is to provide a multi-function heated garment capable of performing multidirectional physical therapy. It can effectively solve the problem that the conventional heated garment has a single structure and function, and the controller used is difficult to quickly identify the quick charge source, and it is difficult to charge the heating load quickly.

In order to achieve the above object, the present invention adopts the following technical solutions:

A multi-function heated garment comprises a garment body, a hood, a heating control device, a quick charge source, and a heating load. A top of the garment body is provided with first electrically conductive buttons. A bottom of the hood is detachably connected to the top of the garment body through a zipper. The bottom of the hood is provided with second electrically conductive buttons. The second electrically conductive buttons are buckled and electrically connected to the first electrically conductive buttons. The heating control device and the quick charge source are arranged in the garment body. The quick charge source and the first electrically conductive buttons are electrically connected to the heating control device. The heating load includes at least one first carbon fiber heating sheet and a second carbon fiber heating sheet. The first carbon fiber heating sheet is arranged inside the garment body and electrically connected to the heating control device. The second carbon fiber heating sheet is arranged inside the hood and electrically connected to the second electrically conductive buttons.

Compared with the prior art, the present invention has obvious advantages and beneficial effects. Specifically, it can be known from the above technical solutions:

1. The first carbon fiber heating sheet and the second carbon fiber heating sheet are arranged inside the garment body and the hood, respectively. The second electrically conductive buttons are buckled and electrically connected to the first electrically conductive buttons. The hood can be connected or disconnected as required. The carbon fiber heating sheets share the quick charge source and the heating control device. It is safe and convenient to use. It can perform multi-directional heating and infrared physical therapy on various parts of the human body. It has various functions and meets the needs of use.

2. The heating control device uses the main control circuit that supports the quick charge (QC) protocol and the quick charge source to complete a handshake communication of the quick charge (QC) protocol and achieve the effects of quickly charging the heating load by the quick charge source after obtaining a successful handshake communication with the quick charge source, so as to reduce the heating time and improve the heating efficiency. Particularly, the heating control device uses the button wake-up circuit to automatically operate the button to wake up the quick charge source to continue working, so as to avoid the quick charge source from entering into the sleep mode, and the wakeup process is automatic and flexible. Besides, the heating control device uses the overvoltage detection circuit and the anti-surge circuit to improve the safety and reliability of the heating control device. Furthermore, the heating control device uses the status indicating light circuit to timely show the operating status of the heating control device and the overall circuit structure is designed skillfully and reasonably to ensure the stability and reliability of the heating control device during use.

DETAILED DESCRIPTION OF THE PREFERRED EMBODIMENTS

Figure 1:
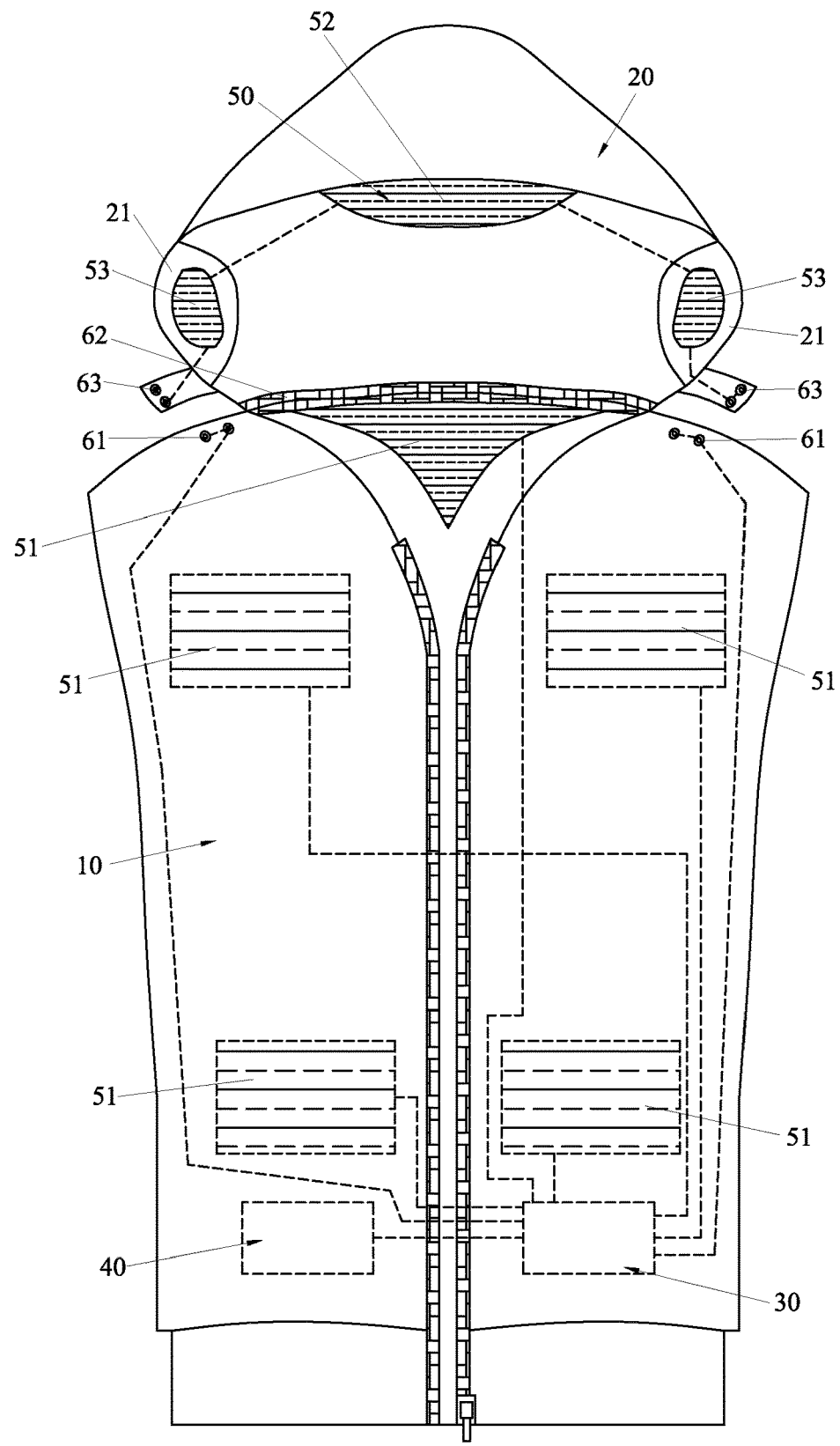
FIG. 1 is a front view according to a preferred embodiment of the present invention.
Figure 2:
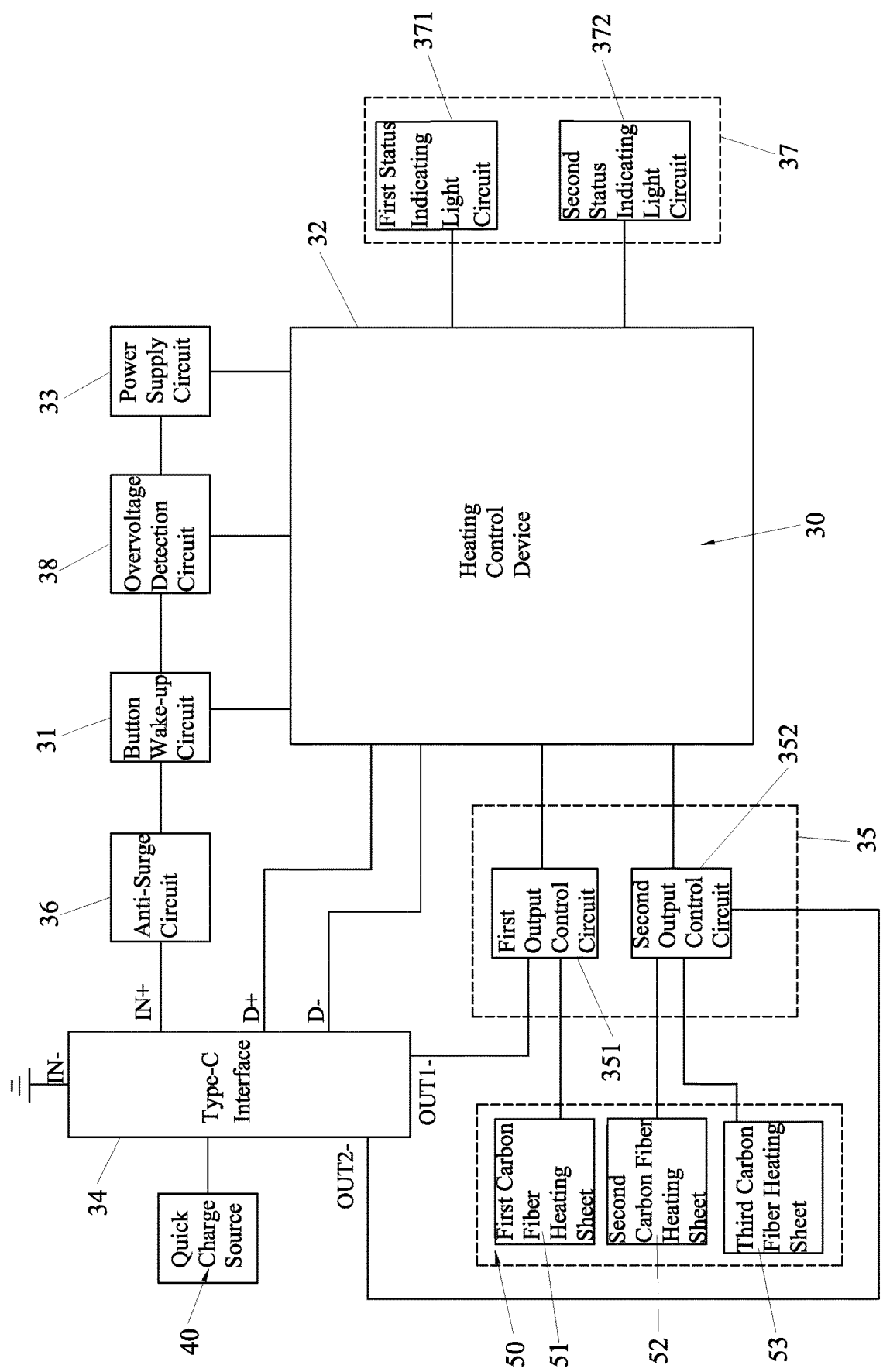
FIG. 2 is a schematic block diagram showing the control principle of the heating control device according to the preferred embodiment of the present invention.
Figure 3:
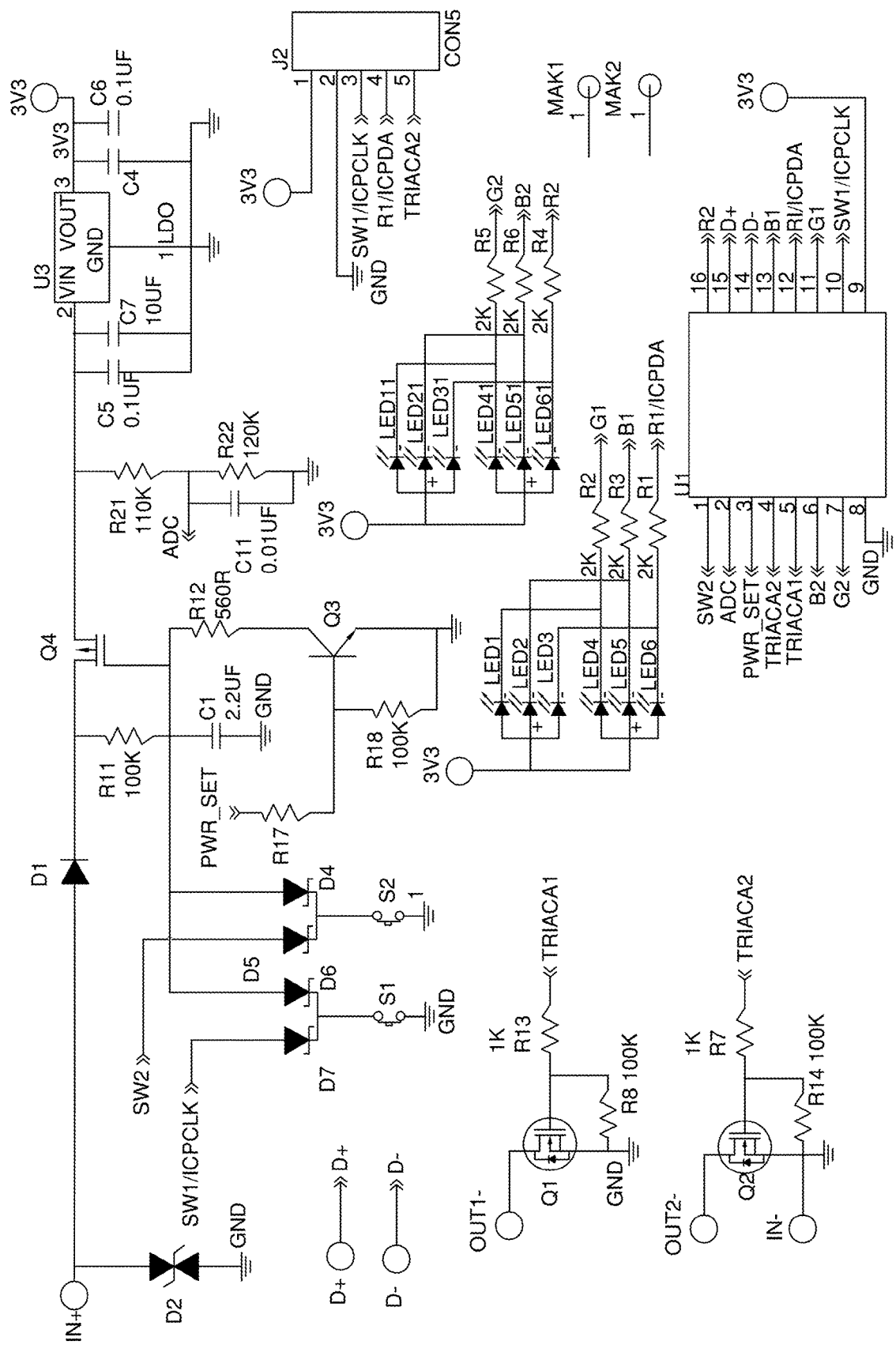
FIG. 3 is a schematic circuit diagram showing the circuit of the heating control device according to the preferred embodiment of the present invention (without showing the quick charge source and the heating load).

FIGS. 1 to 3 show the specific structure of a preferred embodiment of the present invention, comprising a garment body 10, a hood 20, a heating control device 30, a quick charge source 40, and a heating load 50.

The top of the garment body 10 is provided with first electrically conductive buttons 61. The first electrically conductive buttons 61 are arranged in two groups located on the left and right sides of the top of the garment body 10 respectively.

The bottom of the hood 20 is detachably connected to the top of the garment body 10 through a zipper 62. The left and right sides of the hood 20 are provided with earflaps 21. The bottom of the hood 20 is provided with second electrically conductive buttons 63. The second electrically conductive buttons 63 are buckled and electrically connected to the first electrically conductive buttons 61, which facilitates the disassembly and assembly of the hood 20 and reduces the damage and unaesthetic appearance caused by the wire connection. The second electrically conductive buttons 63 are arranged in two groups located on the left and right sides of the bottom of the hood 20, respectively.

Both the heating control device 30 and the quick charge source 40 are arranged inside the garment body 10. Both the quick charge source 40 and the first electrically conductive buttons 61 are electrically connected to the heating control device 30. The heating control device 30 and the quick charge source 40 are located inside the left and right sides of the lower end of the garment body 10, respectively. The heating load 50 includes at least one first carbon fiber heating sheet 51, a second carbon fiber heating sheet 52, and two third carbon fiber heating sheets 53. The first carbon fiber heating sheet 51 is arranged inside the garment body 10 and electrically connected to the heating control device 30. The second carbon fiber heating sheet 52 is arranged inside the hood 20 and electrically connected to the second electrically conductive buttons 63. The two third carbon fiber heating sheets 53 are arranged inside the two earflaps 21 and electrically connected to the second electrically conductive buttons 63, respectively. The first carbon fiber heating sheet 52 includes a plurality of first carbon fiber heating sheets that are respectively located at the cervical spine, back, waist and abdomen positions of the garment body 10 to perform heating and infrared physical therapy on the cervical spine, back, waist, and abdomen of the user.

The heating control device 30 comprises a button wake-up circuit 31 for waking up the quick charge source 40, a main control circuit 32 that supports a quick charge (QC) protocol, a power supply circuit 33 for supplying power to the main control circuit 32, a Type-C interface 34 provided for pairing and coupling the quick charge source 40, and an output control circuit 35 coupled to the heating load 50. The main control circuit 32 is coupled to the output control circuit 35 and the button wake-up circuit 31.

In this embodiment, the quick charge source 40 is a power bank or a charger that supports the quick charge (QC) protocol. Of course, the quick charge source 40 may be other Type-C quick charge source and is not limited by this embodiment.

The Type-C interface 34 comprises a pin IN+, a pin IN−, a pin D+, a pin D− and a pin OUT1−, and a pin OUT2−. The pin IN+ is coupled to the power supply circuit 33 through the button wake-up circuit 31. The pin IN− is grounded. The pin D+ and pin D− are coupled to the main control circuit 32 and completes a handshake communication of a quick charge (QC) protocol with the quick charge source 40. In this embodiment, the pin OUT1− and the pin OUT2− are coupled to the output control circuit 35 for outputting a 20 VDC voltage to the corresponding carbon fiber heating sheets of the heating load 50 to complete a quick charge of the corresponding carbon fiber heating sheets of the heating load 50 under the handshake communication condition.

In this embodiment, the main control circuit 32 comprises a main control chip U1 that supports a QC quick charge protocol (such as QC2.0 protocol, QC3.0 protocol and QC4.0 protocol), and the main control chip U1 has a plurality of main control pins 1 to 16. The main control pin 4 and the main control pin 5 are coupled to the output control circuit 35, respectively. The main control pin 9 is coupled to the power supply circuit 33. The main control pin 14 is coupled to the pin D− of the Type-C interface 34. The main control pin 15 is coupled to the pin D+ of the Type-C interface 34.

In this embodiment, the output control circuit 35 comprises a first output control circuit 351 and a second output control circuit 352. The first output control circuit 351 comprises a resistor R13, a resistor R8 and a MOS tube Q1. The main control pin 4 of the main control circuit 32 is coupled to a gate of the MOS tube Q1 through the resistor R13. The gate of the MOS tube Q1 is coupled to a source of the MOS tube Q1 through the resistor R8. The source of the MOS tube Q1 is grounded. A drain of the MOS tube Q1 is coupled to the pin OUT1−. The second output control circuit 352 comprises a resistor R7, a resistor R14 and a MOS tube Q2. The main control pin 5 of the main control circuit 32 is coupled to a gate of the MOS tube Q2 through the resistor R7. The gate of the MOS tube Q2 is coupled to a source of the MOS tube Q2 through the resistor R14. The source of the MOS tube Q2 is grounded. A drain of the MOS tube Q2 is coupled to the pin OUT2−.

In this embodiment, the button wake-up circuit 31 comprises a button S1, a diode D6, a diode D7, a resistor R11, a resistor R12, a resistor R17, a resistor R18, a capacitor C1, a MOS tube Q4 and a triode Q3. A cathode of the diode D7 and a cathode of the diode D6 are jointly grounded by the button S1. The main control pin 10 of the main control circuit 32 is coupled to an anode of the diode D7. An anode of the diode D6 is coupled to a collector of the triode Q3 through the resistor R12. The anode of the diode D6 is coupled to a gate of the MOS tube Q4. The gate of the MOS tube Q4 is grounded by the capacitor C1. The pin IN+ is coupled to a source of the MOS tube Q4. The source of the MOS tube Q4 and the gate of the MOS tube Q4 are coupled to each other through the resistor R11. A drain of the MOS tube Q4 is coupled to a voltage regulation pin 2 of the power supply circuit 33. The main control pin 3 of the main control circuit 32 is coupled to a base of triode Q3 through the resistor R17. An emitter of the triode Q3 is grounded. The base and emitter of the triode Q3 are coupled to each other through the resistor R18.

In this embodiment, in order to wake up the button conveniently, the button wake-up circuit 31 further comprises a button S2, a diode D4 and a diode D5. A cathode of the diode D4 and a cathode of the diode D5 are jointly grounded by the button S2. The main control pin 1 of the main control circuit 32 is coupled to an anode of the diode D5. An anode of the diode D4 is coupled to the anode of the diode D6.

Since the Type-C interface 34 is plugged in the power bank and situated at a standby mode for a long time, the power bank will be in a sleep mode without outputting power. In this embodiment, regardless of pressing the button S1 or button S2, we can plug in the Type-C interface 34 to wake up the power bank by analogy. For example, pressing the button S1 is used here to illustrate the working principle in this embodiment.

After the button S1 is pressed, the button S1 is grounded instantly, and the MOS tube Q4 is conducted instantly. The main control chip U1 is started immediately to continue sending a signal to trigger the MOS tube Q4 and maintain the conduction of the MOS tube Q4, so that the main control chip U1 has the power continuously and keeps on conducting the MOS tube Q1 and the MOS tube Q2 to charge the heating load 50 quickly.

The power supply circuit 33 comprises a three-terminal voltage regulator U3, a capacitor C4, a capacitor C5, a capacitor C6, a capacitor C7, and a diode D1. The three-terminal voltage regulator U3 comprises a plurality of voltage regulation pins 1 to 3. The voltage regulation pin 1 is grounded. The pin IN+ is coupled to a positive electrode of the diode D1. A negative electrode of the diode D1 is coupled to the voltage regulation pin 2. The voltage regulation pin 2 is coupled to the voltage regulation pin 1 through the capacitor C5. The capacitor C7 is coupled in parallel with both terminals of the capacitor C5. The voltage regulation pin 3 outputs a 3.3 VDC voltage to the main control pin 9 of the main control circuit 32. The voltage regulation pin 3 is coupled to the voltage regulation pin 1 through the capacitor C6. The capacitor C4 is coupled in parallel with both terminals of the capacitor C6.

The present invention further comprises an anti-surge circuit 36, a status indicating light circuit 37, and an overvoltage detection circuit 38 for detecting a voltage between the pin IN+ and the pin IN−.

The pin IN+ is coupled to the voltage regulation pin 2 of the power supply circuit 33 through the anti-surge circuit 36. Preferably, the anti-surge circuit 36 comprises a diode D2 having a terminal coupled to the pin IN+ and the other terminal grounded.

Wherein, a transient voltage suppressor (TVS) diode is a general high-efficiency circuit protection device with an extreme quick response time (sub-nanoscale) and a very high surge absorption capacity. When both terminals of the TVS diode undergo an instant impact of high energy, the TVS diode can change the impedance between the two terminals from high impedance to low impedance and absorb a large instantaneous current and clamp the voltage at both terminals to a predetermined value to protect the subsequent circuits and components from being impacted by the transient high-voltage peak pulse power.

The power supply circuit 33 is electrically coupled to the status indicating light circuit 37, and the status indicating light circuit 37 is coupled to the main control circuit 32.

The status indicating light circuit 37 comprises a first status indicating light circuit 371. The status indicating light circuit 37 comprises a first status indicating light LED1, a status indicating light LED2, a status indicating light LED3, a status indicating light LED4, a status indicating light LED5, a status indicating light LED6, a resistor R4, a resistor R5 and a resistor R6.

Both negative electrodes of the status indicating light LED1 and the status indicating light LED4 are coupled to the main control pin 7 of the main control circuit 32 through the resistor R5. Both negative electrodes of the status indicating light LED2 and the status indicating light LED5 are coupled to the main control pin 6 of the main control circuit 32 of the through the resistor R6. Both negative electrodes of the status indicating light LED3 and the status indicating light LED6 are coupled to the main control pin 16 of the main control circuit 32 through the resistor R4. Six positive electrodes of the status indicating lights LED1 to LED6 are coupled to the power supply circuit 33. In this embodiment, the status indicating light circuit 37 further comprises a second status indicating light circuit 372. The first status indicating light circuit 371 and the second status indicating light circuit 372 are provided for showing the working status of the corresponding carbon fiber heating sheets of the heating load 50. The second status indicating light circuit 372 and the first status indicating light circuit 371 have the same circuit structure. The circuit structure of the second status indicating light circuit 372 is illustrated in FIG. 3.

The overvoltage detection circuit 38 comprises a resistor R21, a resistor R22, and a capacitor C11. The pin IN+ is coupled to the main control pin 2 of the main control circuit 32 through the resistor R21. The main control pin 2 of the main control circuit 32 is grounded by the resistor R22. Both terminals of the resistor R22 are coupled in parallel with the capacitor C11. In this embodiment, the overvoltage detection circuit 38 is disposed between the button wake-up circuit 31 and the power supply circuit 33.

Next, the principle of identifying the quick charge source 40 and charging the heated garment quickly will be elaborated below:

After the Type-C interface 34 is plugged and connected to the quick charge source 40, the quick charge source 40 outputs a standard 5 VDC voltage, and the power supply circuit 33 converts the standard 5 VDC voltage into a 3.3V working voltage which is supplied to the main control chip U1 and the status indicating light circuit 37. After the main control chip U1 is electrically conducted, the main control pin 14 and the main control pin 15 send a handshake signal to the corresponding pin D− and pin D+ of the Type-C interface 34. Once the handshake communication succeeds, the pin OUT1− of the Type-C interface 34 outputs a 20V voltage to the drain of the MOS tube Q1. In the meantime, the pin OUT2− also outputs a 20V voltage to the drain of the MOS tube Q2, so that both MOS tube Q1 and MOS tube Q2 are electrically conducted, and the Type-C interface 34 outputs a 20V voltage to the corresponding heating load 50 for a quick charge and the heating load 50 can be heated quickly.

When this product is in use, the hood 20 can be connected or disconnected as required. When the hood 20 is connected, the second electrically conductive buttons 63 are buckled and electrically connected to the first electrically conductive buttons 61. When the user puts on the heated garment, by controlling the heating control device 30, the quick charge source 40 supplies power to the first carbon fiber heating sheet 51, the second carbon fiber heating sheet 52 and the two third carbon fiber heating sheets 53 of the heating load 50, so that the first carbon fiber heating sheet 51, the second carbon fiber heating sheet 52 and the two third carbon fiber heating sheets 53 generate heat. The first carbon fiber heating sheet 51 generates heat to warm the user's cervical spine, back, waist, abdomen and son on and to perform infrared physical therapy. The second carbon fiber heating sheet 52 generates heat to warm the user's head and to perform infrared physical therapy. The two third carbon fiber heating sheets 53 generate heat to warm the user's ears and to perform infrared physical therapy. Thus, this product can perform multidirectional heating and infrared physical therapy on the human body.

What is claimed is:

1. A multi-function heated garment, comprising a garment body, a hood, a heating control device, a quick charge source, and a heating load; a top of the garment body being provided with first electrically conductive buttons; a bottom of the hood being detachably connected to the top of the garment body through a zipper, the bottom of the hood being provided with second electrically conductive buttons, the second electrically conductive buttons being buckled and electrically connected to the first electrically conductive buttons; the heating control device and the quick charge source being arranged inside the garment body, the quick charge source and the first electrically conductive buttons being electrically connected to the heating control device; the heating load including at least one first carbon fiber heating sheet and a second carbon fiber heating sheet, the first carbon fiber heating sheet being arranged inside the garment body and electrically connected to the heating control device, the second carbon fiber heating sheet being arranged inside the hood and electrically connected to the second electrically conductive buttons;

wherein the heating control device comprises a button wake-up circuit for waking up the quick charge source, a main control circuit that supports a quick charge (QC) protocol, a power supply circuit for supplying power to the main control circuit, a Type-C interface for pairing and coupling the quick charge source, and an output control circuit coupled to the heating load; the main control circuit is coupled to the output control circuit and the button wake-up circuit;

the Type-C interface includes a pin (IN+), a pin (IN−), a pin (D+), and a pin (D−) and a pin (OUT−), the pin (IN+) is coupled to the power supply circuit through the button wake-up circuit, the pin (IN−) is grounded, the pin (D+) and pin (D−) are coupled to the main control circuit and completes a handshake communication of the quick charge (QC) protocol with the quick charge source, and the pin OUT1− is coupled to the output control circuit to quickly charge the heating load under the condition of the handshake communication.

2. The multi-function heated garment as claimed in claim 1, wherein left and right sides of the hood are provided with earflaps, the heating load further includes two third carbon fiber heating sheets, and the two third carbon fiber heating sheets are arranged inside the two earflaps and electrically connected to the second electrically conductive buttons, respectively.

3. The multi-function heated garment as claimed in claim 1, wherein the first carbon fiber heating sheet includes a plurality of first carbon fiber heating sheets that are located at a cervical spine position, a back position, a waist position and an abdomen position of the garment body, respectively.

4. The multi-function heated garment as claimed in claim 1, wherein the main control circuit comprises a main control chip (U1) having a plurality of main control pin (1) and pin (16);

the main control pin (4) and the main control pin (5) are coupled to the output control circuit respectively, the main control pin (9) is coupled to the power supply circuit, the main control pin (14) is coupled to the pin (D−) of the Type-C interface, and the main control pin (15) is coupled to the pin (D+) of the Type-C interface.

5. The multi-function heated garment as claimed in claim 1, wherein the output control circuit comprises a resistor (R13), a resistor (R8) and a MOS tube (Q1), the main control circuit is coupled to a gate of the MOS tube (Q1) through the resistor (R13), the gate of the MOS tube (Q1) is coupled to a source of the MOS tube (Q1) through the resistor (R8), the source of the MOS tube (Q1) is grounded, and a drain of the MOS tube (Q1) is coupled to the pin (OUT1−).

6. The multi-function heated garment as claimed in claim 1, wherein the Type-C interface further comprises a pin (OUT2−);

the output control circuit further comprises a resistor (R7), a resistor (R14) and a MOS tube (Q2); the main control circuit is coupled to a gate of the MOS tube (Q2) through the resistor (R7), the gate of the MOS tube (Q2) is coupled to a source of the MOS tube (Q2) through the resistor (R14), the source of the MOS tube (Q2) is grounded, and a drain of the MOS tube (Q2) is coupled to the pin (OUT2−).

7. The multi-function heated garment as claimed in claim 1, wherein the button wake-up circuit comprises a button (S1), a diode (D6), a diode (D7), a resistor (R11), a resistor (R12), a resistor (R17), a resistor (R18), a capacitor (C1), a MOS tube (Q4), and a triode (Q3);

a cathode of the diode (D7) and a cathode of the diode (D6) are jointly grounded by the button (S1), the main control circuit is coupled to an anode of the diode (D7), an anode of the diode (D6) is coupled to a collector of the triode (Q3) through the resistor (R12), the anode of the diode (D6) is coupled to a gate of the MOS tube (Q4);

the gate of the MOS tube (Q4) is grounded by the capacitor (C1), the pin (IN+) is coupled to a source of the MOS tube (Q4), the source of the MOS tube (Q4) and the gate of the MOS tube (Q4) are coupled to each other through the resistor (R11), a drain of the MOS tube (Q4) is coupled to the power supply circuit;

the main control circuit is coupled to a base of triode (Q3) through the resistor (R17), an emitter of the triode (Q3) is grounded, and the base and the emitter of the triode (Q3) are coupled to each other through the resistor (R18).

8. The multi-function heated garment as claimed in claim 1, further comprising an overvoltage detection circuit for detecting a voltage between the pin (IN+) and the pin (IN−);

wherein the overvoltage detection circuit comprises a resistor (R21), a resistor (R22) and a capacitor (C11), the pin (IN+) is coupled to the main control circuit through the resistor (R21), the main control circuit is grounded by the resistor (R22), and both terminals of the resistor (R22) are coupled in parallel with the capacitor (C11).

9. The multi-function heated garment as claimed in claim 1, further comprising an anti-surge circuit and a status indicating light circuit, the pin (IN+) being coupled to the power supply circuit through the anti-surge circuit, the power supply circuit being electrically coupled to the status indicating light circuit, the status indicating light circuit being coupled to the main control circuit.

* * * * *